United States Patent [19]

Rose et al.

[11] Patent Number: 4,629,466
[45] Date of Patent: Dec. 16, 1986

[54] OXIDATION HAIR DYES COMPRISING BIS-(2,4-DIAMINOPHENYL)-ALKANES AS COUPLING COMPONENTS

[75] Inventors: David Rose, Hilden; Edgar Lieske, Düsseldorf, both of Fed. Rep. of Germany

[73] Assignee: Henkel Kommanditgesellschaft auf Aktien, Dusseldorf-Holthasen, Fed. Rep. of Germany

[21] Appl. No.: 465,666

[22] Filed: Feb. 10, 1983

[30] Foreign Application Priority Data

Sep. 25, 1982 [DE] Fed. Rep. of Germany ....... 3235615

[51] Int. Cl.$^4$ .......................... A61K 7/13; C07C 87/52
[52] U.S. Cl. ............................................. 8/408; 8/416; 8/421; 8/424; 564/305
[58] Field of Search .................. 8/406, 421, 424, 426, 8/408; 564/305, 330

[56] References Cited

U.S. PATENT DOCUMENTS

| | | | |
|---|---|---|---|
| 3,452,038 | 6/1969 | Randall et al. | 564/330 X |
| 3,558,703 | 1/1971 | Adam et al. | 564/330 X |
| 4,314,809 | 2/1982 | Rose et al. | 564/305 X |

FOREIGN PATENT DOCUMENTS

| | | |
|---|---|---|
| 365785 | 12/1922 | Fed. Rep. of Germany . |
| 1959462 | 6/1971 | Fed. Rep. of Germany . |

OTHER PUBLICATIONS

Helv. Chim. Acta 22 (1939), 970–978.

*Primary Examiner*—Robert V. Hines

[57] ABSTRACT

This invention is directed to compositions of the developer-coupler type of the dyeing of hair consisting essentially of bis-(2,4-diaminophenyl)-alkanes or salts thereof as coupling components and, as developer components, the conventional components used in oxidation dyes.

9 Claims, No Drawings

OXIDATION HAIR DYES COMPRISING BIS-(2,4-DIAMINOPHENYL)-ALKANES AS COUPLING COMPONENTS

FIELD OF THE INVENTION

This invention is directed to oxidation hair dyes. More specifically, this invention is directed to bis-(2,4-diaminophenyl)-alkanes and their use as coupling components in oxidation hair dyes.

BACKGROUND OF THE INVENTION

Dyes known as oxidation dyes, which are produced by oxidative coupling of a developer component with a coupling component, are preferred due to their intense colors, the mild reaction conditions under which they are formed, and their very good fastness properties. Nitrogen bases such as primary aromatic amines with an additional hydroxyl or unsubstituted or substituted amino group in p- or o-position, diaminopyridine derivatives, 4-amino-pyrazolone derivatives, heterocyclic hydrazone derivatives, and tetraaminopyrimidines are generally used as developer substances. Phenols, m-phenylenediamine derivatives, naphthols, resorcinol derivatives, and pyrazolones are useful as coupling components.

Good oxidation dyestuff components must meet the following requirements:

They must produce the desired color nuances in sufficient intensity during oxidative coupling with the respective developer or coupling component. Also, they must possess a capacity for being absorbed by human hair without excessive coloring of the scalp. In addition, they should be toxicologically and dermatologically safe.

The production of the strongest possible color shades closely corresponding to the natural hair color nuances is also important. Furthermore, the general stability of the dyestuffs produced as well as their fastness to light and to washing and their thermostability, have very special significance for the prevention of color shifts from the original color nuance or even a change in color to different shades. In addition, in the hair dyeing field there is always an interest in new oxidation dye components that can be combined with the known dye components to produce new color nuances of cosmetic value.

Tetraamino derivatives of diphenyl, diphenylmethane, and diphenylethane are known as oxidation dye intermediate products from German Pat. No. 365,785. However, the color shades obtainable with these substances are unsatisfactory in their purity and intensity and in their resistance to heat and cold-waving of the hair. For example, bis-(2,4-diaminophenyl)-methane and 1,2-bis-(2',4'-diaminophenyl)-ethane produce brown-gray to brown-black nuances with p-toluylenediamine that take on a dirty, impure brown shade under the influence of heat or thioglycolate solutions.

Bis-(2,4-diaminophenoxy)-alkanes and their use as oxidation dye intermediate products are known from U.S. Pat. No. 4,314,809. However, the creation of coupling components with even better toxicological and dermatological properties remains a desirable goal.

Thus, the search for suitable oxidation hair dyes includes the task of finding the proper components that meet the above-mentioned prerequisites in an optimal fashion.

OBJECTS OF THE INVENTION

It is an object of the invention to provide bis-(2,4-diaminophenyl)-alkane compounds.

It is also an object of the invention to provide agents for the oxidative dyeing of hair that are based upon bis-(2,4-diaminophenyl)-alkane compounds as coupling components.

It is a further object of the invention to provide a process for dyeing hair wherein a novel hair dyestuff is employed.

These and other objects of the invention will become more apparent in the discussion below.

DETAILED DESCRIPTION OF THE INVENTION

Applicants have found novel hair dyestuffs that satisfy the above-mentioned requirements. The hair dyestuffs are based upon oxidation dyes comprising bis-(2,4-diaminophenyl)-alkanes of the formula

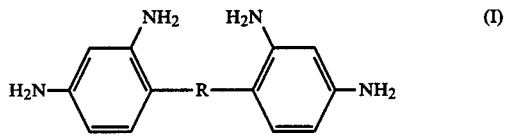

wherein R represents an alkylene having 3 or 4 carbon atoms, or salts thereof with inorganic or organic acids, as coupling component, and, as developer component, one or more the conventional developer substances used in oxidation hair dyes. Such hair dyestuffs can meet the above-mentioned requirements to an especially high degree and consequently represent especially valuable combinations in the area of oxidation hair dyes.

The compounds of Formula I are novel and thus represent an additional aspect of the invention. Two compounds of Formula I, namely, 1,3-bis-(2',4'-diaminophenyl)-propane and 1,4-bis-(2',4'-diaminophenyl)-butane, are considered to be especially suitable coupling substances. The compounds of Formula I can be prepared by procedures analogous to syntheses known from the literature by catalytic hydrogenation of the respective bis-(2,4-dinitrophenyl)-alkanes.

The novel coupling substances of Formula I are suitable for a large number of different developer systems, and especially intense pure green and blue nuances are particularly obtained when aromatic or heterocyclic diamines are used as developer substances. Examples of such developer components include p-phenylenediamine, p-toluylenediamine, N-methyl-p-phenylenediamine, N,N-dimethyl-p-phenylenediamine, N,N-diethyl-2-methyl-phenylenediamine, N-ethyl-N-(2-hydroxyethyl)-p-phenylenediamine, chloro-p-phenylenediamine, N,N-bis-(2-hydroxyethyl)-p-phenylenediamine, methoxy-p-phenylenediamine, 2,5-diaminoanisole, 2,6-dichloro-p-phenylenediamine, 2-chloro-6-bromo-p-phenylenediamine, 2-chloro-6-methyl-p-phenylenediamine, 6-methoxy-3-methyl-p-phenylenediamine, N-ethyl-N-(2-hydroxyethyl)-p-phenylenediamine, N-(2-methoxyethyl)-p-phenylenediamine, and N-(2-hydroxypropyl)-p-phenylenediamine and other compounds of this type which also contain one or more additional functional groups such as hydroxyl groups, amino groups, or -NHR or -NR$_2$ groups in which R represents an alkyl with 1 to 4 carbon atoms or a hydroxyalkyl with from 2 to 4 carbon atoms. Diaminopyridine derivatives, heterocyclic hydrazone derivatives such as 1-methylpyrrolidon-(2)-hydrazone, 4-amino-pyrazolone derivatives such as 4-amino-1-phenyl-3-carbamoyl-pyrazolone-5, N-butyl-N-sulfobutyl-p-phenylenediamine, and tetraaminopyrimidine derivatives comprise additional examples of useful developer components.

Upon the use of the compounds according to the invention, that is, the bis-(2,4-diaminophenyl)-alkanes of Formula I and the salts thereof, as coupling components together with developers generally used for oxidation hair dyes, the resulting hair dyes yield very intense shades in the green to deep blue range, and thus such use represents a considerable expansion of the possibilities in oxidation hair dyeing. In addition, the resulting hair dyes according to the invention are characterized by great purity and very good fastness characteristics of the resulting colors as well as by resistance to light, heat, and the influence of cold-waving treatments based upon mercaptans.

The bis-(2,4-diaminophenyl)-alkanes of Formula I to be used as coupling components according to the invention can be used either as such or in the form of their salts with inorganic or organic acids, for example, as hydrochlorides, sulfates, phosphates, acetates, propionates, lactates, or citrates. In addition, the bis-(2,4-diaminophenyl)-alkanes of Formula I can be used together with additional, known coupling substances for hair dye products, such as, for example, naphthols; resorcinol derivatives such as 2-methylresorcinol or 4-chlororesorcinol; pyrazolones; or m-phenylenediamine derivatives. Also, conventional, directly attaching dyes such as, for example, nitrophenylenediamine derivatives, can be added to modify the color nuances.

In the hair dystuffs according to the invention, the coupling and developer components generally are used in approximately equimolar amounts. Although the equimolar use proves suitable, it is not disadvantageous to add the coupling component in a certain excess or deficiency. For example, the coupling and developer components can be present in a molar range of from about 2:1 to 1:2, a 10% or less excess or deficiency being preferred.

In addition, it is not necessary that the developer component and the coupling substance are homogeneous or pure products. On the contrary, the developer component may consist of mixtures of the developer compounds to be used according to the invention, and the coupling substance may be in the form of mixtures of bis-(2,4-diaminophenyl)-alkanes or salts thereof according to the invention.

The oxidative coupling, that is, the development of the dye, can in principle be carried out with atmospheric oxygen, as is done with other oxidation hair dyestuffs also. However, chemical oxidation agents are advantageously employed. Particularly suitable as such oxidation agents are hydrogen peroxide or its adducts with urea, melamine, or sodium borate as well as mixtures of such hydrogen peroxide adducts with potassium peroxydisulfate.

The bis-(2,4-diaminophenyl)-alkanes of Formula I offer the advantage as coupler component that they yield satisfactory dye results even with oxidative coupling by atmospheric oxygen. If, however, a lightening effect on the hair is desired together with the dye, the simultaneous use of oxidation agents is necessary.

For the preparation of the hair dyes according to the invention, the oxidation dye intermediate products are incorporated into suitable cosmetic preparations such as, for example, creams, emulsions, gels, foam aerosols, or foaming solutions containing tensides, such as shampoos, or other products suitable for application to the hair. Conventional components of such cosmetic preparations include, for example, wetting and emulsifying agents such as anionic, nonionic, or ampholytic tensides, for example, sulfates of fatty alcohols, alkane sulfonates, $\alpha$-olefin sulfonates, polyglycol ether sulfates of fatty alcohols, adducts of ethylene oxide onto fatty alcohols, fatty acids, or alkyl phenols, sorbitan fatty acid esters, partial glycerides of fatty acids, and alkanolamides of fatty acids; thickeners such as methyl or hydroxyethyl cellulose, starch, fatty alcohols, liquid paraffin, or fatty acids; perfume oils; and hair-conditioning and grooming additives such as water-soluble cationic polymers, protein derivatives, pantothenic acid, or cholesterol.

The above-mentioned additives are added in the amounts normal for these purposes. For example, wetting and emulsifying agents can be present in concentrations of from about 0.5 to 30 percent by weight, preferably from about 1 to 15 percent by weight, and thickeners can be present in concentrations of from about 0.1 to 25 percent by weight, preferably from about 1 to 15 percent by weight, based, respectively, upon the total weight of the hair dye preparation. The concentration of the oxidation dye intermediate products, that is, the coupler/developer combination, in hair dye preparations is from about 0.05 to 5 percent by weight, preferably from about 1 to 3 percent by weight, based upon the total weight of the hair dye preparation.

A hair dye according to the invention can be applied in a weakly acid, neutral, or particularly alkaline medium at a pH of from 8 to 10, regardless of whether it is in the form of a solution, an emulsion, a cream, or a gel. The application temperatures range from about 15° to 40° C. After the dye is allowed to react for a sufficient time, usually approximately 30 minutes, the preparation is removed by rinsing from the dyed hair. The hair is then washed with a mild shampoo and dried. Shampooing would be unnecessary if the hair dye preparation itself, for example, a coloring shampoo, has a high tenside content. The hair, which can be any color or length, can be either "live" hair or hair that has been cut, such as that in a wig.

The colors that can be achieved with the hair dyes according to the invention cover a broad spectrum of green to deep blue shades with the use of various developer and coupling components. The colors obtained show good fastness to light, shampooing, and abrasion, and they are easily stripped with reducing agents.

The following examples are intended to illustrate the invention and are not to be construed as limiting the invention thereto.

EXAMPLES

I. PREPARATION OF BIS-(2,4-DIAMINOPHENYL)-ALKANES ACCORDING TO THE INVENTION

A. 1,3-Bis-(2',4'-diaminophenyl)-propane tetrahydrochloride (a) Preparation of 1,3-bis-(2',4'-dinitrophenyl)-propane Five grams of 1,3-diphenylpropane were added dropwise, at a temperature of from −5° C. to −10° C., to 50 ml of nitric acid with a density of 1.52 g/ml. The solution was warmed to approximately 20° C. over a period of two hours. The reaction mixture was then poured over ice water and filtered, and the residue was washed neutral. The residue was purified by boiling with ethanol and crystallization, once from acetic acid and twice from methyl ethyl ketone. The yield was 2.4 gm. The product had a melting point of 168°–170° C.

(b) Hydrogenation

A quantity of 2.3 gm of bis-(2',4'-dinitrophenyl)-propane was dissolved in 100 ml of ethanol and, after addition of palladium on activated charcoal (5% by weight Pd), the resulting solution was catalytically hydrogenated in a hydrogen atmosphere. After the completion of the hydrogen uptake, the catalyst was removed by filtration, and the filtrate was acidified with concentrated hydrochloric acid and evaporated to dryness. The product was obtained in the form of white crystals that melt at approximately 306° C., with decomposition.

B. 1,4-Bis-(2', 4'-diaminophenyl)-butane tetrahydrochloride (a) Preparation of 1,4-bis-(2',4'-dinitrophenyl)-butane The above compound was prepared according to the procedure disclosed by Fr. Fichter and H. Stenzl, Helv. Chim. Acta, Vol. 22 (1939), page 975.

(b) Hydrogenation

Four grams of 1,4-bis-(2',4'-dinitrophenyl)-butane were dissolved in 100 ml of ethanol and, after addition of palladium on activated charcoal (5% by weight Pd), the resulting solution was catalytically hydrogenated in a hydrogen atmosphere. After the completion of the hydrogen uptake, the catalyst was removed by filtration, and the filtrate acidified with concentrated hydrochloric acid and evaporated to dryness. The product was obtained in the form of beige-colored crystals that melt, with decomposition, at approximately 310° C.

II. OXIDATION HAIR DYE TESTING

The compounds prepared above as well as two comparison compounds were used as coupling components in oxidation hair dyes. The comparison coupling components were as follows:

C*: bis-(2,4-diaminophenyl)-methane
D*: 1,2-bis-(2',4'-diaminophenyl)-ethane

The following substances were used as developer components:

E-1: p-phenylenediamine
E-2: p-toluylenediamine
E-3: N-methyl-p-phenylenediamine
E-4: 2-chloro-p-phenylenediamine
E-5: 2,5-diaminoanisole
E-6: N-ethyl-N-(2-hydroxyethyl)-p-phenylenediamine
E-7: N-butyl-N-sulfobutyl-p-phenylenediamine
E-8: N,N-bis-(2-hydroxyethyl)-p-phenylenediamine
E-9: N-(2-methoxyethyl)-p-phenylenediamine
E-10: N-(2-hydroxypropyl)-p-phenylenediamine
E-11: 2,4,5,6-tetraaminopyrimidine
E-12: p-aminophenol Procedure The hair dyes according to the invention were used in the form of a cream emulsion. For this, 0.01 mol of each of the developer substances and coupling substances listed in the table below were worked into an emulsion containing 10 parts by weight of fatty alcohols having 12 to 18 carbon atoms,
10 parts by weight of fatty alcohol sulfate (sodium salt) having 12 to 18 carbon atoms, and
75 parts by weight of water.

Then the pH of the emulsion was adjusted to 9.5 with ammonia, and the emulsion was made up to 100 parts by weight with water. Oxidative coupling was carried out with a 9% hydrogen peroxide solution acting as oxidation agent, 10 parts by weight of the hydrogen peroxide solution being added to 100 parts by weight of the emulsion.

After addition of the oxidation agents, the particular dyeing cream, with additional oxidation agent, was applied to standardized human hair which was 90% gray and which had not been specially pretreated, and the cream was left on the hair for thirty minutes at about 35° C. After completion of the dyeing process, the hair was washed out with a conventional commerical shampoo and dried. The colorations obtained by this process are compiled in the table below:

TABLE

| Example | Coupling Agent | Developer | Shade of Dyed Hair After Oxidation with 9% H$_2$O$_2$ Solution |
|---|---|---|---|
| 1 | A | E-1 | black blue |
| 2 | A | E-2 | ink blue |
| 3 | A | E-3 | black blue |
| 4 | A | E-4 | black blue |
| 5 | A | E-5 | ink blue |
| 6 | A | E-6 | nordic blue |
| 7 | A | E-7 | matt blue |
| 8 | A | E-8 | ink blue |
| 9 | A | E-9 | black blue |
| 10 | A | E-10 | ink blue |
| 11 | A | E-11 | dark green |
| 12 | A | E-12 | violet brown |
| 13 | B | E-2 | dark blue |
| 14 | C* | E-2 | brown gray |
| 15 | D* | E-2 | black gray |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A composition of the developer-coupler type for the dyeing of the hair, consisting essentially of at least one compound of the formula

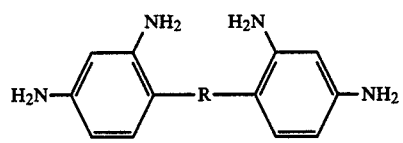

wherein R represents an alkylene having 3 or 4 carbon atoms, or a salt thereof with an inorganic or organic acid, as coupling component, and, as developer component, one or more of the conventional developer components used in oxidation dyes.

2. The composition of claim 1, wherein R represents an n-propylene or n-butylene.

3. The composition of claim 1, wherein the developer components are aromatic or heterocyclic diamines.

4. The composition of claim 1 which additionally contains conventional additives selected from the group consisting of conventional couplers and conventional directly absorbing dyes.

5. The composition of claim 1, wherein the composition comprises from about 0.05 to 5 percent by weight of developer/coupler combination.

6. The composition of claim 5, wherein the composition comprises from about 1 to 3 percent by weight of developer/coupler combination.

7. A process for the dyeing of human hair comprising applying to said hair, at temperatures ranging substantially from about 15° to 40° C. for a time sufficient to effect dyeing through oxidation, an effective amount of the developer/coupler composition of claim 1 in an aqueous medium.

8. The process for the dyeing of hair of claim 7, wherein the oxidation is effected by the action of a chemical oxidation agent.

9. A compound of the formula

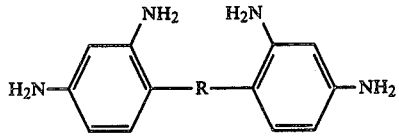

wherein R represents an alkylene having 3 or 4 carbon atoms.